United States Patent [19]

Hüschelrath

[11] Patent Number: 4,689,996
[45] Date of Patent: Sep. 1, 1987

[54] METHOD AND DEVICE FOR TESTING ELECTRICALLY CONDUCTING OBJECTS BY MEANS OF ULTRA-SONICS

[75] Inventor: Gerhard Hüschelrath, Laufach, Fed. Rep. of Germany

[73] Assignee: Nukem GmbH, Hanau, Del.X

[21] Appl. No.: 719,957

[22] Filed: Apr. 4, 1985

[30] Foreign Application Priority Data

Apr. 12, 1984 [DE] Fed. Rep. of Germany ....... 3413787

[51] Int. Cl.$^4$ ............................................ G01N 29/04
[52] U.S. Cl. ........................................ 73/643; 73/598; 73/644
[58] Field of Search .................. 73/597, 598, 643, 644, 73/635

[56] References Cited

U.S. PATENT DOCUMENTS

| 4,348,903 | 9/1982 | Sato et al. ............................. 73/643 |
| 4,449,411 | 5/1984 | Suhr et al. ............................. 73/643 |
| 4,452,086 | 6/1984 | Huschelrath et al. ................. 73/643 |

Primary Examiner—Howard A. Birmiel
Attorney, Agent, or Firm—Cushman, Darby & Cushman

[57] ABSTRACT

The subject of the invention is a method and device for non-destructive testing of electrically conducting objects (10) by means of penetrating ultra-sonic waves, whereby the ultra-sonics signals are electro-dynamically generated. While being tested the object is located in a magnetic field. The probes (30, 32) arranged on diametrically opposite sides of the object (10) are set at the smallest possible constantly maintained distance from the surface. The signals used for detecting the flaw are corrected so that any variations in the thickness of the object (10) in the area of the probes (30, 32) are taken into account.

9 Claims, 5 Drawing Figures

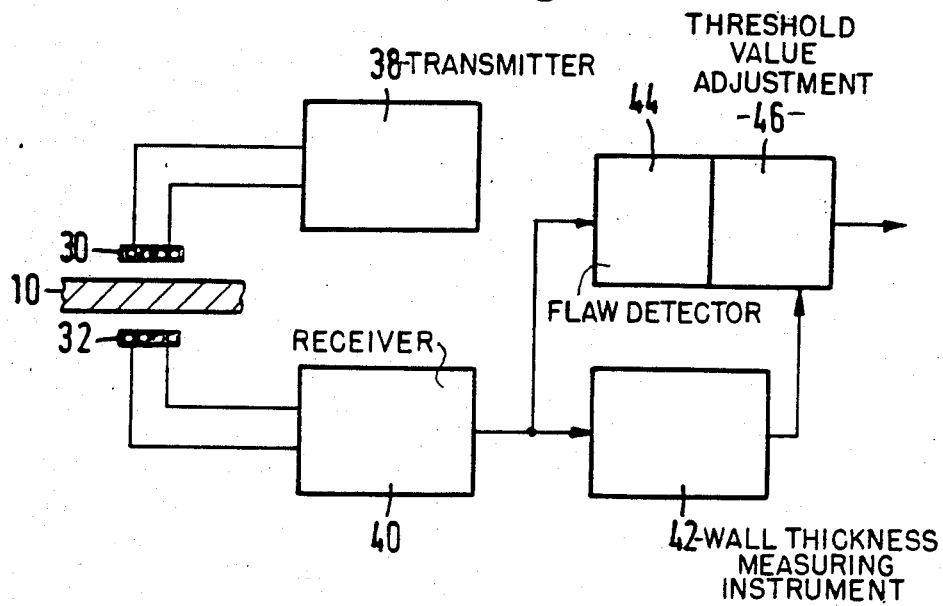
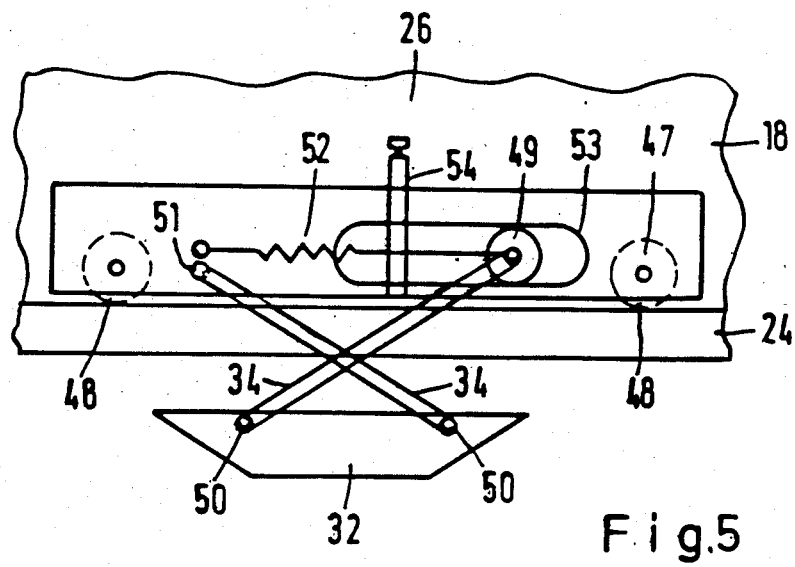

METHOD AND DEVICE FOR TESTING ELECTRICALLY CONDUCTING OBJECTS BY MEANS OF ULTRA-SONICS

The invention relates to a method and a device intended for non-destructive flaw testing on electrically conducting objects by means of electro-dymanically generated ultra-sonic signals, whereby transmitter and receiver probe units are provided between the poles of a magnet, and on diameterically opposite sides of the object.

STATE OF THE PRIOR ART

High-frequency alternating currents are generated in the transmitter probes of electro-dynamic transducers, and induce eddy currents in the conducting objects. The surface of the test piece is subjected to a force resulting from the interaction of the eddy currents flowing in it and a magnetic field. This excites electro-dynamic ultra-sonic waves. Flat spiral-type coils are frequently used to induce the eddy currents. The ultra-sonic amplitudes depend on the distance of the transmitter coils to the surface of the object. There is a marked fall-off in the amplitude as the distance between the transmitter coil and the surface of the test piece increases. Coils arranged in a magnetic field are used to pick up the ultra-sonic waves. The voltage induced in the receiver coils has the same frequency as the ultra-sonic oscillation. The efficiency of conversion of electrical energy into acoustic energy and vice versa is low. Due to the consequent low sensitivity, and because of the great effect the measured signal the spacing between the test piece and the transmitter coil has on the level of the measured signal, non-destructive testing of objects using electro-dynamically generated ultra-sonic waves is recommended at best for determining wall thicknesses. Until now full ultra-sonic penetration testing techniques with electro-dynamic excitation have been regarded as unachievable, since the variations in clearance between the tested object and the transmitter and receiver probes exceed the measurement effect by significantly more than double. Although an electro-dynamic ultra-sonic transducer with its probes arranged on diametrically opposite sides of the object undergoing test can be recognized from the drawing of the No. DE-02 30 42 645, there is nevertheless no indication of a realistic possibility of detecting flaws in workpieces with sufficient accuracy using the full ultra-sonic penetration method. One the contrary, one should comment of the probes, noting their arrangement in a fixed manner relative to the tested object, their construction and the material used.

When testing objects, for example with piezo-electric probes coupled to the surface of the object by means of a water-bath, the thicknesses of the test pieces can be determined only by using considerable means. Due to the path-dependent attenuation, the thickness of the test pieces affects the amplitude of the measurement signals. Changes in the thickness of the test piece consequently influence the measurement signal amplitude, and represent a source of disturbance.

OBJECTS OF THE INVENTION

The invention is aimed at further developing a device of the type initially described, such that defects in objects can be detected to sufficient accuracy using the full ultra-sonic penetration method by electro-dynamic excitation.

SOLUTION OF THE PROBLEM

According to the invention the task is achieved in that during testing the magnetic field strengths in the object are held constant. Furthermore, the transmitter and receiver probes are each maintained at a constant distance from the surface of the object, and that variations of the thickness of the object between the probes is taken into account in the signals picked up to detect the flaw. In this way the effect on the measurement signal of the spacing between the surface of the object and the EDW probes is considerably reduced.

When penetration by means of electro-dynamic excitation the wall thickness is found without additional probes, since the ultra-sonic effect is first generated in the surface of the test piece, and then detected again. The invention utilizes this effect in order to correct the echo signals via the known ultra-sonic attenuation in the object. Variations in the wall thickness are thereby eliminated as noise sources when penetrating with ultra-sonic noise.

A device for carrying out this method can be seen in FIG. 2. It can detect, for example, fractures, cavities, etc., in the test piece using the ultra-sonic method. There is no adverse effect on the measurement signals if there is an offset angle between the ultra-sonic probes and the objects to be tested. In this respect the device thus has a significant advantage over ultra-sonic oscillators, which are coupled to test pieces via water-baths. In the case of water coupling angular offset of the test piece causes a change in the sonic penetration angle. This results in noise signals.

The magnetic induction in the air gap between the magnet in which the object is tested should preferably be set to a value of 10 kGauss, or higher.

The invention's design permits the transmitter probes and the receiver probes to oscillate to and fro at a constant distance from each other over the surface of the object to be tested. With this device one can test objects with surface areas which are large compared to the size of the testing probes.

BRIEF DESCRIPTION OF THE DRAWINGS

Further details, advantages and features of the invention are clear from the following description of the embodiments illustrated by a drawing:

The following are shown by:

FIG. 4 A circuit arrangement for generation and processing of test signals, and

FIG. 5 A holder for a receiving transducer, side elevation.

DETAILED DESCRIPTION OF THE INVENTION

Figure 1:
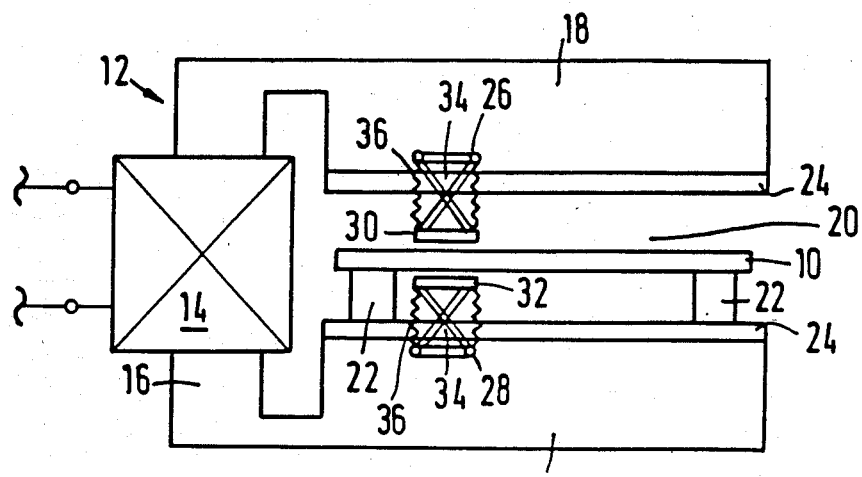
FIG. 1 Front elevation of a device for testing electrically conductive objects by means of ultra-sonics FIG. 2 Plan elevation of the device shown in FIG. 1
Figure 2:
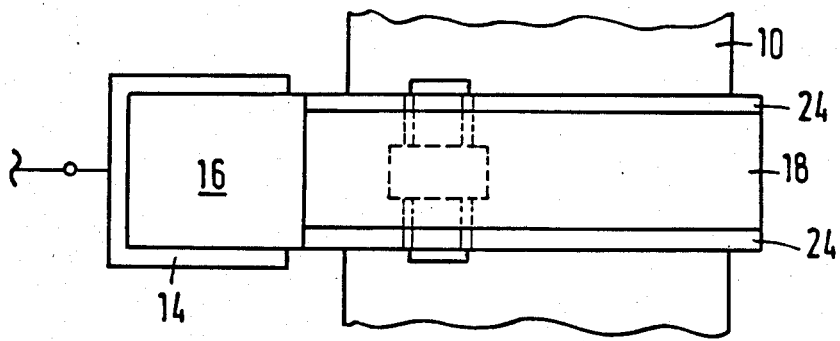
Figure 3:
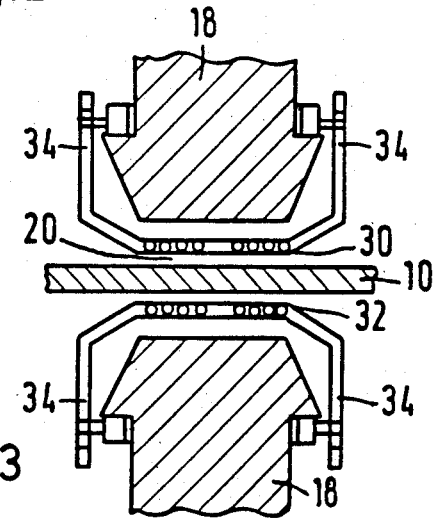
FIG. 3 Details in cross-section of the device illustrated in FIG. 1

A device for non-destructive testing of electrically conducting objects 10, of which is shown in FIGS. 1–4. The device features an electro-magnet 12 containing a yoke 16 equipped with a coil 14 and two arms 18. The arms 18 run parallel to one another over a long distance; between them is an air gap 20 through which the test object 10—an iron plate for example—is passed.

The object 10 can be transported on rollers 22. Extending over the full length on the air gap 20 side of the arms 18 are rail-like projections 24.

Arranged on the rail-like projections 24 are holders 26, 28 each of which carries a transmitter probe 30 and a receiver probe 32 for ultra-sonic waves. The transmitter and receiver probes 30, 32 are coils subjected to transmission and receiption currents. The transmitter and receiver probes 30, 32 are located in the air gap 20. The transmitter probe 30 is arranged on one side of the object 10 at a short distance from its surface; the receiver probe 32 is located at a short distance from object 10 on the diametrically opposite side. As described in detail below, holders 26, 28 have rollers running on the rail-like projections 24 and are connected to X-crossed supporting bars 34. Attached to the ends of these bars are the transmitter or receiver, 30 or 32 respectively. The distance between the surface of the object 10 and the transmitter or receiver probe 30, 32 respectively can be adjusted by means of the supporting bars 34. The transmitter probe 30 and the receiver probe 32 are each held in respective positions by springs 36.

The electro-magnet 12 generates a stationary magnetic field of constant field strength in the air gap 20. The test object 10 can be para-, dia- or ferro-magnetic. In the case of para-, and dia-magnetic objects 10 the same field strength and magnetic flux must be provided in order to generate ultra-sonic waves of a specific amplitude, such as in ferro-magnetic objects. The excitation winding of the magnet is designed so that the field strength losses can be compensated by the shift in the hysteresis curve.

The transmitter probe 30 is connected to a transmitter 38 for high-frequency alternating currents. The high-frequency alternating current flowing in the coil of transmitter probe 30 induces in object 10 high-frequency eddy currents, which are influenced by the magnetic field generated by the electro-magnet. Under the effect of the magnetic field and of the magnetic induction present in the surface of the object 10, the eddy currents cause ultra-sonic waves, which propagate through the object 10. Because the vector of the magnetic field is perpendicular to the surface of the object 10, transverse waves occur with their frequency matching the currents in the transmitter probes 30.

The transverse ultra-sonic waves are converted into eddy currents on the opposite side of the object 10 due to the influence of the magnetic field. These eddy currents then induce voltages in the receiver probe 32, which are fed to the input of the receiver 40. The receiver probe 32 is at a small constant distance from the surface of the object 10. So as to a maintain as constant a spacing as possible from the surface of the object 10, it is—as previously mentioned—advantageous to press the receiver probe 32 against the surface by means of spring force. The same applies to the transmitter probe 30. This measure avoids noise signals induced by changes in the spacing.

The receiver 40 provides a gain of approximately 30 dB in the received signal. Circuited behind it is a wall thickness measuring instrument 42, and a flaw detector 44 providing an output signal if the input signal exceeds a preselected threshold value. The threshold value can be changed by means of an adjustment circuit 46 controlled by the output signal of the wall thickness measuring instrument 42. For practical purposes a visual display unit—not illustrated—is connected behind the flaw detector 44.

The receiver 40, the wall thickness measuring instrument 42, the flaw detector 44 and the adjustment circuit 46 preferably take the form of plug-in modules; they are mounted on a rack together with the visual display unit and a power supply unit for the electro-magnet 12. Type FDW-01, UL-20, SE-03, M-01/S-01, Z-01 units produced by the NUKEM Company, D-6450 Hanau/-Main 11, Federal Republic of Germany, can be practically used as receiver 40, wall thickness measuring instrument 42, flaw detector 44 and adjustment circuit 46.

The supporting bars are each connected to the transmitter probe 30 or receiver probe 32 respectively by hinge pins 50 at one end, as shown in FIG. 5. The transmitter and receiver probes are each coils. One supporting rod 34 is hinged at its opposite end by a pin 51 to a carriage 47 containing rollers 48, which are guided on the rail-like projections 24. The other supporting rod 34 is hinged at its other end to another roller 49, which can move longitudinally in a slot 53. Slot 53 extends lengthwise along the carriage 47. The axis of roller 49—not further detailed—is connected at one end to a spring 52 the other end of which is located near hinge pin 51. Spring 49 thus applies tension to the roller 49 approximately in opposition to hinge pin 51. Arranged in slot 53 is a variable stop 54, which has a locking screw not described in further detail.

Spring 52 pulls the roller 49 up to the stop 54. Adjusting the position of stop 54 in slot 53 allows the space between the ends of the supporting bar 34 and consequently the opening angle between the bars 34 to be set to a desired value. Thus an appropriate adjustment of the stop allows the clearance between the receiver probe 32 and the surface of the test object 10 to be precisely determined. Attachment to supporting bars 34 prevents the receiver probe 32 from twisting. The clearances can be set to very small values. Even if the receiver probe 32 touches the surface of the object 10 this will not affect the motion along the surface of the object, since expansion of the spring can deflect the receiver probe 32 toward the rail-like projections 24. In the case of an appropriately robustly built transmitter or receiver probe, the stop 54 can be adjusted such that the transmitter and receiver probes 30, 32 respectively, each lightly contact the surface of the object 10 if this should be necessary to obtain a high signal-to-noise ratio for detecting specific flaws or wall thickness. Primarily suitable for this method are objects with smooth surfaces.

Ultra-sonic testing of object 10 is carried out with the transmitter and receiver probes 30, 32. In order to cover the different sections of broad objects 10, the transmitter and receiver probes 30, 32 are moved in sequence by shifting the holder 26 into different positions to allow a full-coverage test of the object 10 over its complete width. Object 10 is then moved on by an increment larger than one test zone. After that testing is carried out over the width of the object 10, whereby the transmitter and the receiver transducers 30, 32 are moved along the rail-like projections into adjoining positions. The ultra-sonic tests are now carried out in these positions by the transmitter 38 feeding high-frequency alternating current into transmitter probe 30. At the same time the ultra-sonic waves generated by transmitter probe 30 in conjunction with the magnetic field themselves generate high-frequency voltages in the receiver probe 32, which are evaluated to determine wall thickness and to detect flaws.

The wall thickness measuring instrument 42 determines the wall thickness by using the passage time of the ultra-sonic waves from one surface of the object 10 to the other surface, and generates an output signal proportional to the wall thickness. This wall thickness-proportional signal can be generated without using additional probes. The attenuation of the ultra-sonic signal in object 10 is highly dependent on the thickness of the wall. So as not to falsely interpret as material flaws the effects on the received signals caused by the change in the wall thickness, the wall thickness effect is eliminated in the flaw detector by matching up to the threshold value decisive to flaw detection. Changes in the wall thickness can thus no longer act as noise signals to distort the measurement values.

The flaw detector 44 determines the absolute signal amplitude of the first or several echo signals, compares them with the set threshold value and, in the event of not reaching or exceeding it, signals this at the output as a flaw. The threshold value is determined from the wall thickness and the known attenuation of ultra-sonic signals in a flawless object. If a rapid test is required on the respective objects 10 it is also possible to use several transmitter and receiver probes 30, 32 next to one-another.

Of considerable significance is a constant relative magnetic induction based on the value of the reference measurement in the surface region of the object undergoing test 10. Assuming that the electro-magnet 12 generates a magnetic field of constant field strength in air gap 20, the previously described condition for dia- and para-magnetic objects 10 is achieved in a simple manner, regardless of the wall thickness, in that the distance between the arms 18 is maintained at the same value. Only the clearance between the transmitter and receiver probes 30, 32 must be adjusted to the actual wall thickness of the object 10.

The absolute magnetic field strength may vary from measuring task to measuring task, since the measurement parameters are calibrated. It is important for the relative magnetic field strength not to vary during a measurement. If the air gap changes simply due to the thickness variation of the test piece, this is recognized by the wall thickness measurement channel.

In ferro-magnetic objects a constant relative magnetic induction in the surface region is achieved for large, different wall thicknesses by matching the air gap with adapter pieces. The gauge of the air gap 20—i.e., the free air space between the arms 18—is kept approximately constant, regardless of the thickness of the object's wall. Adjustment of the clearance between transmitter and receiver 30, 32 to the respective wall thickness of the object under test is also necessary. Shifting the object 10 toward the arm 18 and, if needs be, an angular offset does not cause distortion of the measured value.

The device described above can be advantageously used for ultra-sonic testing of objects 10 with walls of constant thickness at least over large sections. For example, plates, sheets, tapes and tubes can all be tested for flaws on the surface and on the inside of the walls.

The circuit arrangement illustrated in FIG. 4 is calibrated using objects with precisely known dimensions. The values obtained when testing objects then relates to the values generated by calibrated objects.

I claim:

1. An apparatus for performing non-destructive testing of an electroconductive plane object, said apparatus comprising:
   a magnet being substantially U-shaped, with the poles of said magnet extending along opposite arms of the U-shape, the object to be tested being placed between the poles of the magnet
   an electrodynamic transmitting probe being arranged between a first surface of the test object and one of the poles of said magnet;
   a coordinated receiving probe being arranged between a second surface of the test piece and the other pole of said magnet;
   said transmitting and receiving probes being moved synchronously oscillatorily over the test object along the poles at a constant preset distance to the respective first and second surfaces; and
   a flaw detector and a wall thickness measuring instrument for generating an output signal proportional to the thickness of the wall connected to the receiving probe, the output signal being fed to an adjustment circuit by which a response threshold value of the flaw detector can be varied.

2. An apparatus according to claim 1, further comprising rail-shaped projections along the longitudinal direction of the poles and associated respective holding devices for the transmitting and receiving probes.

3. An apparatus according to claim 2, wherein the holding device encloses X-crossed supporting bars, at one end of which the transmitting or receiving probe is arranged and the other end of which is connected to a carriage travelling along a guide, where one of the supporting bars with one end is swivellingly supported by the carriage, while the other supporting bar with one of its ends is displaceably arranged in the carriage in a longitudinal direction of the carriage and is affected by tension directed toward the first supporting bar.

4. An apparatus according to claim 3, wherein a stop is arranged in shifting paths of the end of the supporting bar, the stop being adjustable to different distances to the end of the other supporting bar.

5. An apparatus according to claim 1, wherein the magnetic induction in an air gap between the poles of the magnet is at least ten KGauss.

6. An apparatus for performing non-destructive testing of an electroconductive plane object, said apparatus comprising:
   a magnet being substantially U-shaped, with the poles of said magnet extending along opposite arms of the U-shape, the object to be tested being placed between the poles of the magnet
   an electrodynamic transmitting probe being arranged between a first surface of the test object and one of the poles of said magnet;
   a coordinated receiving probe being arranged between a second surface of the test piece and the other pole of said magnet;
   said transmitting and receiving probes being moved synchronously oscillatorily over the test object along the poles at a constant preset distance to the respective first and second surfaces; and
   rail-shaped projections along the longitudinal direction of the poles and associated respective holding devices for the transmitting and receiving probes;
   wherein the holding device encloses X-crossed supporting bars, at one end of which the transmitting or receiving probe is arranged and the other end of which is connected to a carriage travelling along a guide, where one of the supporting bars with one end is swivellingly supported by the carriage, while the other supporting bar with one of its ends is displaceably arranged in the carriage in a longitudinal direction of the carriage and is affected by tension directed toward the first supporting bar.

7. An apparatus according to claim 6, wherein a stop is arranged in shifting paths of the end of the supporting bar, the stop being adjustable to different distances to the end of the other supporting bar.

8. An apparatus according to claim 6, wherein the magnetic induction in an air gap between the poles of the magnet is at least ten KGauss.

9. An apparatus according to claim 6, further comprising a flaw detector and a wall thickness measuring instrument for generating an output signal proportional to the thickness of the wall connected to the receiving probe, the output signal being fed to an adjustment circuit by which a response threshold value of the flaw detector can be varied.

* * * * *